United States Patent
Jones et al.

(10) Patent No.: US 10,632,289 B2
(45) Date of Patent: Apr. 28, 2020

(54) SECUREMENT DEVICE WITH ATTACHABLE MEMBERS FOR USE WITH A CATHETER

(71) Applicant: The Johns Hopkins University, Baltimore, MD (US)

(72) Inventors: Cameron C. Jones, Pikesville, MD (US); Clifford R. Weiss, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 8 days.

(21) Appl. No.: 15/118,556

(22) PCT Filed: Feb. 17, 2015

(86) PCT No.: PCT/US2015/016209
§ 371 (c)(1),
(2) Date: Aug. 12, 2016

(87) PCT Pub. No.: WO2015/123684
PCT Pub. Date: Aug. 20, 2015

(65) Prior Publication Data
US 2017/0043130 A1  Feb. 16, 2017

Related U.S. Application Data

(60) Provisional application No. 61/940,547, filed on Feb. 17, 2014.

(51) Int. Cl.
*A61M 25/02* (2006.01)

(52) U.S. Cl.
CPC ....... *A61M 25/02* (2013.01); *A61M 2025/028* (2013.01); *A61M 2025/0246* (2013.01); *A61M 2025/0253* (2013.01)

(58) Field of Classification Search
CPC .......... A61M 25/02; A61M 2025/0246; A61M 2025/028; A61M 2025/0206;
(Continued)

(56) References Cited

U.S. PATENT DOCUMENTS

| | | | | |
|---|---|---|---|---|
| 6,213,979 B1 * | 4/2001 | Bierman | ............... | A61M 25/02 128/DIG. 26 |
| 6,736,797 B1 * | 5/2004 | Larsen | ................. | A61M 5/158 604/167.05 |

(Continued)

FOREIGN PATENT DOCUMENTS

| | | |
|---|---|---|
| EP | 1757323 A1 | 2/2007 |
| WO | 91-16939 A1 | 11/1991 |

OTHER PUBLICATIONS

Written Opinion of the International Searching Authority dated May 18, 2015 in corresponding PCT/US2015/016209.

(Continued)

*Primary Examiner* — Nathan R Price
*Assistant Examiner* — Melissa A Snyder
(74) *Attorney, Agent, or Firm* — Mintz Levin Cohn Ferris Glovsky and Popeo, P.C.; Peter F. Corless; Carolina E. Säve

(57) ABSTRACT

The present invention describes a securement device that maintains proper placement of a percutaneous catheter and incorporates a universal fitting for the attachment of various, interchangeable, active and passive technologies. The securement device includes a unique catheter hub that enables attachment of active technology to provide diagnostic, therapeutic, and monitoring applications of physiologic, anatomic, and other clinically relevant properties or conditions. The securement device also includes a primary semi-flexible polymeric retention member (the "base") positioned atop, or integrated with, a thin flexible adhesive pad. The adhesive pad has a first surface with an adhesive substrate (Continued)

and a second surface configured to receive the base. The hub is received within the base and a cap is used to secure the hub to the base.

13 Claims, 10 Drawing Sheets

(58) Field of Classification Search
CPC .... A61M 2025/0233; A61M 2025/024; A61M 2025/0245; A61M 2025/0293; A61M 39/0247; A61M 2039/0261
See application file for complete search history.

(56) References Cited

U.S. PATENT DOCUMENTS

| | | | |
|---|---|---|---|
| 7,153,291 B2 | 12/2006 | Bierman | |
| 7,220,246 B2 * | 5/2007 | Raulerson | A61M 25/02 604/174 |
| 8,016,793 B2 | 9/2011 | Wright et al. | |
| 9,642,988 B2 * | 5/2017 | Mizoguchi | A61M 25/02 |
| 2005/0107743 A1 * | 5/2005 | Fangrow, Jr. | A61M 5/158 604/164.01 |
| 2008/0132848 A1 * | 6/2008 | Wright | A61M 25/01 604/174 |
| 2009/0182283 A1 | 7/2009 | Sloan | |
| 2012/0277670 A1 * | 11/2012 | Goetz | A61M 25/02 604/93.01 |

OTHER PUBLICATIONS

International Searching Report dated May 18, 2015 in corresponding PCT/US2015/016209.

* cited by examiner

SECUREMENT DEVICE WITH ATTACHABLE MEMBERS FOR USE WITH A CATHETER

CROSS REFERENCE TO RELATED APPLICATION

This application is a National Phase of PCT Application No.: PCT/US2015/016209, filed Feb. 17, 2015 and claims priority to and the benefit of U.S. Patent Application No. 61/940,547 filed in the United States Patent and Trademark Office on Feb. 17, 2014, the entire contents of which are incorporated herein by reference.

FIELD OF THE INVENTION

The present invention relates generally to medical devices. More particularly, the present invention relates to a securement device with attachable members for use with a catheter.

BACKGROUND OF THE INVENTION

Many patients with chronic diseases or who are critically ill require frequent administration of fluids for nutritional or medicinal purposes. These medications are oftentimes delivered through an intravenous catheter such as a central venous catheter (CVC), peripherally inserted central catheter (PICC), and midline catheter, which provide vascular access and can be kept in place for durations lasting several days up to several months. Modern medical catheters that have a portion of the catheter body extending outside the patient ("percutaneous") consist of an indwelling portion, and an external region primarily acting as a conduit to the indwelling portion. Many catheters are multi-luminal, where each lumen may serve different functions depending on anatomic location and/or dictated interventional therapy. External to the patient, the multi-luminal catheter bifurcates into single lumen lines, where the distal ends of said lines consist of a standard medical fitting (e.g., luer) for connecting infusion lines or various medical equipment, and a clamp to prevent fluid movement and air embolism when the catheter is not being accessed. The site of bifurcation is often called the "hub" or "transition" and is traditionally a molded stock connecting the indwelling catheter to the external extension(s), residing immediately adjacent to the insertion site.

Following placement of the intravascular catheter, it is often necessary to secure the catheter to the patient when used for extended periods of time to prevent axial displacement of the catheter with regards to its anatomical position. Securement of the catheter is generally accomplished by one of three means, which all involve the catheter hub: suturing the catheter hub to the patient's skin through eyelets in the "wings" extending from the molded hub; applying tape in a crisscross fashion over the catheter hub, securing the hub to the patient's skin; or placing the hub in a semi-flexible securement device which is held to the patient's skin by an adhesive base and comprises a shaped region for receiving the catheter hub. The securement methods prevent axial movement of the catheter and resist snagging or tugging of external extensions with environmental articles. These securement devices are inexpensive units that can be easily removed for cleaning of the insertion site and are discarded periodically (i.e., following daily maintenance).

Medical catheters, including urinary catheters, are manufactured using polymeric compounds such as silicone, polyethylene, polyurethane, and polytetrafluoroethylene to increase biocompatibility and longevity of use. Despite precautions, catheter-related bloodstream and catheter-associated urinary tract infections are a frequent and growing concern, having significant consequences to patient morbidity and mortality, and greatly taxing to healthcare resources. Infections stem from bacterial adsorption on the catheter surface, giving way to a prolific growth of a highly antibiotic-resistant community of cells called biofilm. Once biofilm begins to develop, antibiotic efficacy decreases due to the protective nature of the biofilm matrix which inhibits penetration of the biocide. The predominant sources of these infectious bacteria that colonize on the catheter surface are external to the patient, and, for intravenous catheters particularly, originate at the skin surface (at the insertion site) or through the frequent access of the luer fittings—which occur every time a healthcare professional connects a fluid line, collects blood samples, or attaches any number of monitoring or other devices that utilize the luer connection. Each procedure that accesses these central lines poses a potential risk to contamination.

Most of the protocols of prevention and treatment secondary to the imbued biocompatibility of the catheter involve daily cleaning of insertion site and locking the intraluminal space with potent antibiotics or anti-thrombogenic agents. Some healthcare centers utilize needleless connectors and other accessories attached at the extravascular portion of the catheter to act as an additional barrier to external contamination. In large part, technologies that attach directly to the extravascular, longitudinal portion of the catheter tube, utilize no particular feature of the catheter other than the uniformity of said catheter. For example, clamshell-like attachments are attached at any portion of the circumferential catheter, imparting the respective technology to the catheter as a non-discriminate single entity.

There are a number of technologies designed to sterilize and/or disinfect catheters, including administering germicidal ultraviolet (UV) light and ultrasound. UV light is often used commercially in microbiology labs for sterilizing labware, and long-wave ultrasound (20-100 kHz) may provide concomitant efficacy with antibiotics against bacteria through several biological mechanisms. Traditional methods for applying acoustic energy to a catheter surface require placing a large transducer above (external) to the intravascular region with the acoustic source perpendicular to the catheter. Such systems require large ultrasonic equipment and a technician to sweep the transducer head over the entire length of the implanted catheter.

It would therefore be advantageous to provide a securement device to which various active and passive technologies can be quickly and easily attached to the catheter.

SUMMARY OF THE INVENTION

The foregoing needs are met by the present invention which provides a securement device for use with a percutaneous catheter including a base defining a top side and a bottom side. The bottom side is configured for attachment to a surface, and the top side defines retention walls in a predetermined geometry. The securement device also includes a catheter hub having an outer wall defining the predetermined geometry, such that the catheter hub is held within the retention walls of the base.

In accordance with an aspect of the present invention, the base defines alignment members for further constraining movement of the catheter hub. The bottom side of the base is attachable to a surface with an adhesive pad. The base is formed from a semi-flexible, polymeric material. Additionally, the device includes securement assembly configured to lock the catheter hub to the base. The securement assembly includes a cap and a locking ring. The locking ring defines geometry configured to interlock with geometry defined by the base. The cap further defines a groove in which the locking ring is disposable. The locking ring is freely rotatable within the groove.

In accordance with another aspect of the present invention, the present invention provides a method of attaching a securement device for use with a percutaneous catheter. The method includes disposing a catheter hub between retention walls of a base having a top side and a bottom side. The top side of the base defines the retention walls in a predetermined geometry. In addition, the catheter hub is locked to the base using a securement assembly that has a cap and a ring and then the bottom side of the base is attached to a surface.

Further, the locking of the catheter hub to the base includes locking securement tabs of the cap to the retentive walls of the base to hold the cap to the securement device and to hold the catheter hub between the securement assembly and the base. The bottom side of the base is attachable to a surface with an adhesive pad. The securement assembly is also coupled to the base using any known coupling mechanism such as a push-and-twist, screw type, snap-fitting, slotted mechanism, and a frictional fit. The ring of the cap that is secured to the base, defines geometry configured to interlock with geometry defined by the base.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention describes a securement device that maintains proper placement of a percutaneous catheter and incorporates a universal fitting for the attachment of various, interchangeable, active and passive technologies. The securement device includes a unique catheter hub that enables attachment of active technology to provide diagnostic, therapeutic, and monitoring applications of physiologic, anatomic, and other clinically relevant properties or conditions. The securement device also includes a primary semi-flexible polymeric retention member (the "base") positioned atop, or integrated with, a thin flexible adhesive pad. The adhesive pad has a first surface with an adhesive substrate and a second surface configured to receive the base. The hub is received within the base and a cap is used to secure the hub to the base.

Figure 1:
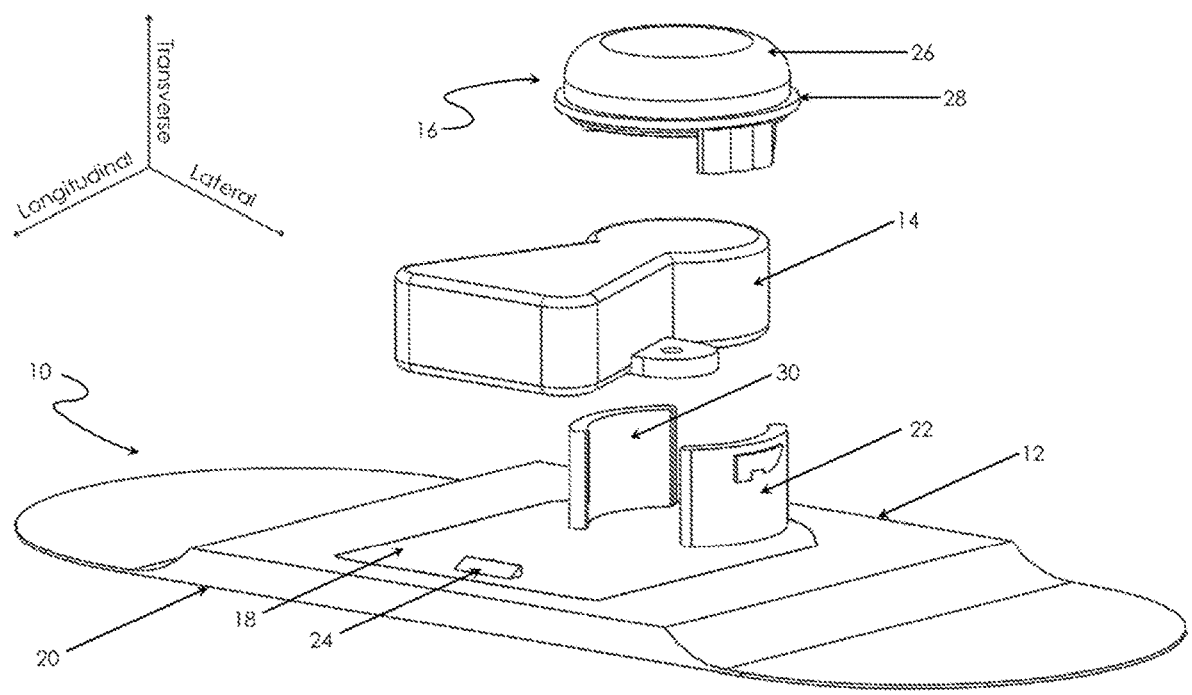
FIG. 1 illustrates an exploded view of a catheter securement device according to an embodiment of the present invention.

FIG. 1 illustrates an exploded view of the retention components of the securement device, according to an embodiment of the present invention. As illustrated in FIG. 1 the securement device 10 includes a securement base 12, a catheter hub 14 that fits into the securement base 12, and a securement assembly 16 that locks the catheter hub 14 into the securement base 12. The securement base 12 includes a top surface 18 and a bottom surface 20. Vertical retentive members 22 extend up from the top surface 18 of the securement base 12, in order to hold the catheter hub in a desired place on the top surface 18 of the securement base 12. Additionally, the securement base includes alignment tabs 24 to provide additional planar stability and orientation of the catheter hub 14. The alignment tabs 24 can take on a generally symmetrical or generally asymmetrical arrangement to ensure proper axial alignment of the catheter, complementing the vertical retentive members 22. The securement assembly 16 includes a dome-shaped cap 26 and ring 28 that attach to the securement base over the catheter hub 14 to provide for three-axis stability to retention of the catheter hub 14.

Further with respect to FIG. 1, the vertical retentive members 22 define a geometry that matches at least part of an outer geometry of the catheter hub 14, thereby creating a frictional fit between the securement base 12 and the catheter hub 14. The catheter hub 14 can be encompassed either partially or completely by the vertical retentive members 22. The vertical retentive members 22 can also define varying heights around the outer geometry of the catheter hub 14. Alternately, the catheter hub 14 can be positioned immediately adjacent to the vertical retentive members 22, such that transitions in shape along a longitudinal axis provide partial alignment. The vertical retentive members 22 can define a generally annular shaped region 30 with a through slit in order to accommodate catheter components. The annular shaped region 30 is orthogonal to a longitudinal axis of the catheter and/or hub and prevents longitudinal movement. The securement base 12, catheter hub 14, and securement assembly 16 are all preferably formed from a thermoplastic or other biocompatible and lightweight material, such that the securement device 10 is inexpensive and disposable in order to further efforts to minimize bacteria or other environmental contamination.

With respect to the securement assembly 16 illustrated in FIG. 1, the securement assembly 16 can couple to the securement base 12 using any number of attachment schemes known to or conceivable by one of skill in the art. Exemplary attachment schemes include push-and-twist, screw type, snap-fitting, slotted mechanism, or frictional fit, with the catheter hub 14 cooperatively disposed between the vertical retentive members 22 and the securement assembly 16. Additionally, the securement assembly 16 can use any combination of bosses and recesses, magnetic, adhesive, hook-and-loop, or other forms of interlocking means. Preferably, the ring 28 of the securement assembly 16 is a freely-rotating member disposed within a circumferential groove within the cap 26, such that the cap assembly may be placed on the securement base and the interlocking mechanism employed while maintaining relative position of the dome-shaped member. While it is generally expected the interlocking means will utilize a rotationally symmetric means, the retentive region of the securement base 12 and cap 26 may be of ellipsoid, rectangular, or other geometrical shape. The vertical retentive members 22, including any alignment tabs 24, may be either bosses or recesses for receiving the catheter hub with a conformed relationship. The interlocking mechanism is not intended to require the use of any surgical tools such as hemostats or sutures.

Additionally with respect to FIG. 1, an underside of the cap 26 is flush with an upper surface of the catheter hub 14. In another embodiment, the cap contains a V-shaped base that, when fully attached through the interlocking mechanism, clamps the inner catheter lumen to prevent the movement of fluids. The cap 26 is an interchangeable member that acts as a passive restraint and completes the securement device 10. The securement base 12 acts as a universal receiver for caps having different purposes. For securement applications, the vertical retentive members 22 of the securement base 12 are sufficient to maintain axial stability while caps of different utility are being exchanged. Caps may be disposable or reusable, may contain proprietary elements, and may be intermittently utilized for different therapeutic or functional applications. Some of the modular cap assemblies may include active elements, or features requiring a power source. Power sources for driving active caps may be in the form of a battery or capacitor existing within the cap, or provide power originating from a cable.

Figure 2:
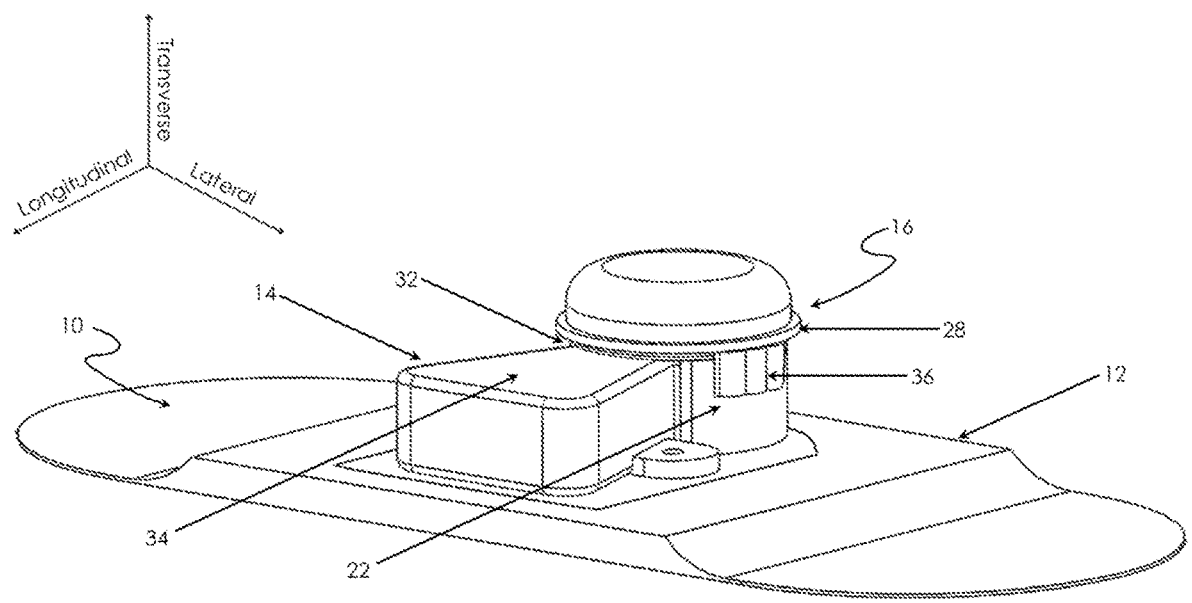
FIG. 2 illustrates a perspective view of an assembled catheter securement device according to an embodiment of the invention.

FIG. 2 illustrates a perspective view of an assembled catheter securement device according to an embodiment of the invention. As illustrated in FIG. 2, a particular portion 32 of the catheter hub 14 is secured in a transverse direction by the locking function of the securement assembly 16, wherein the ring 28 is secured to the securement base 12, and where the securement assembly 16 is flush with an upper surface 34 of the catheter hub 14. Securement tabs 36 lock to the vertical retentive members 22 of the securement base 12 in order to hold the cap to the securement device 10, and to sandwich the catheter hub 14 between the securement assembly 16 and the securement base 12.

Figure 3:
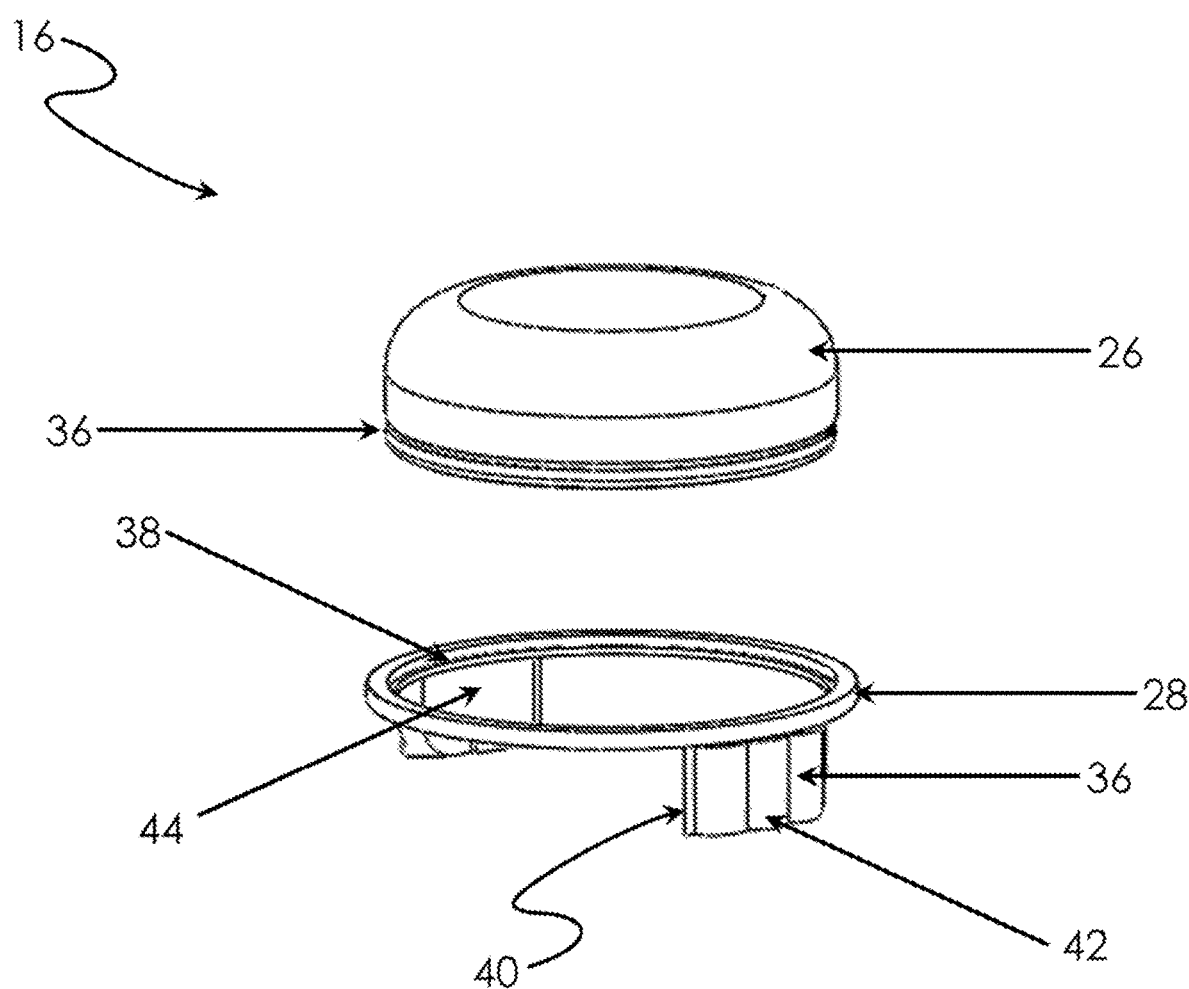
FIG. 3 illustrates an exploded view of a cap and ring assembly according to an embodiment of the present invention.

FIG. 3 illustrates an exploded view of a cap and ring assembly according to an embodiment of the present invention. The securement assembly 16 includes cap 26 and ring 28, where the cap 26 includes a circumferential recessed groove 36 into which at least an inner edge 38 of the ring 28 can be disposed. The ring 28 is unrestricted in rotational access relative to the position of the cap 26. The inner surface of the securement tabs 36 of the ring 28 define a locking mechanism 40 for further securely holding the securement assembly 16 to the securement base 12. As noted above, the locking mechanism 40 can use any number of attachment schemes known to or conceivable by one of skill in the art to couple the securement assembly 16 to the securement base 12. Exemplary attachment schemes include push-and-twist, screw type, snap-fitting, slotted mechanism, or frictional fit, with the catheter hub 14 cooperatively disposed between the vertical retentive members 22 and the securement assembly 16. Additionally, the securement assembly 16 can use any combination of bosses and recesses, magnetic, adhesive, hook-and-loop, or other forms of interlocking means.

Figure 4:
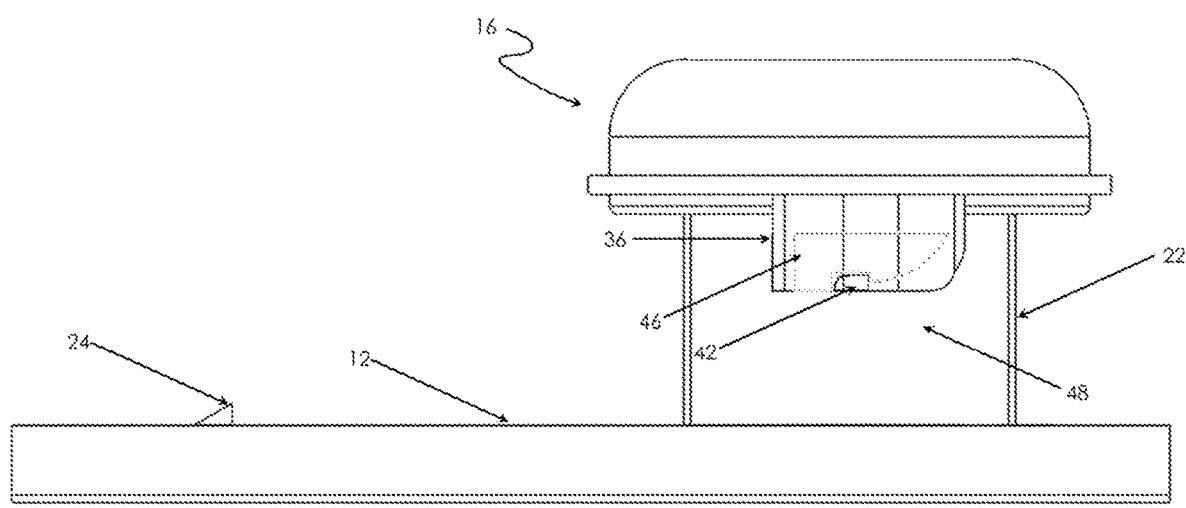
FIG. 4 illustrates a side view of a locking mechanism for a cap and ring assembly according to an embodiment of the present invention.

FIG. 4 illustrates a side view of a locking mechanism for a cap and ring assembly according to an embodiment of the present invention. The exemplary locking mechanism 40 of the securement assembly 16 is shown engaging with the vertical retentive members 22 of the securement base 12. The locking mechanism 40 includes a tab 42 on an inner surface 44 of the securement tab 36 that engages with a boss 46 on an outer surface 48 of the vertical retentive members 22. In this example, the securement assembly 16 is removed with a push and turn method. Also illustrated is alignment tab 24 that fits into a recess on the distal portion of the catheter hub 14 and provides proper alignment and additional stability of the catheter hub 14.

Figure 5:
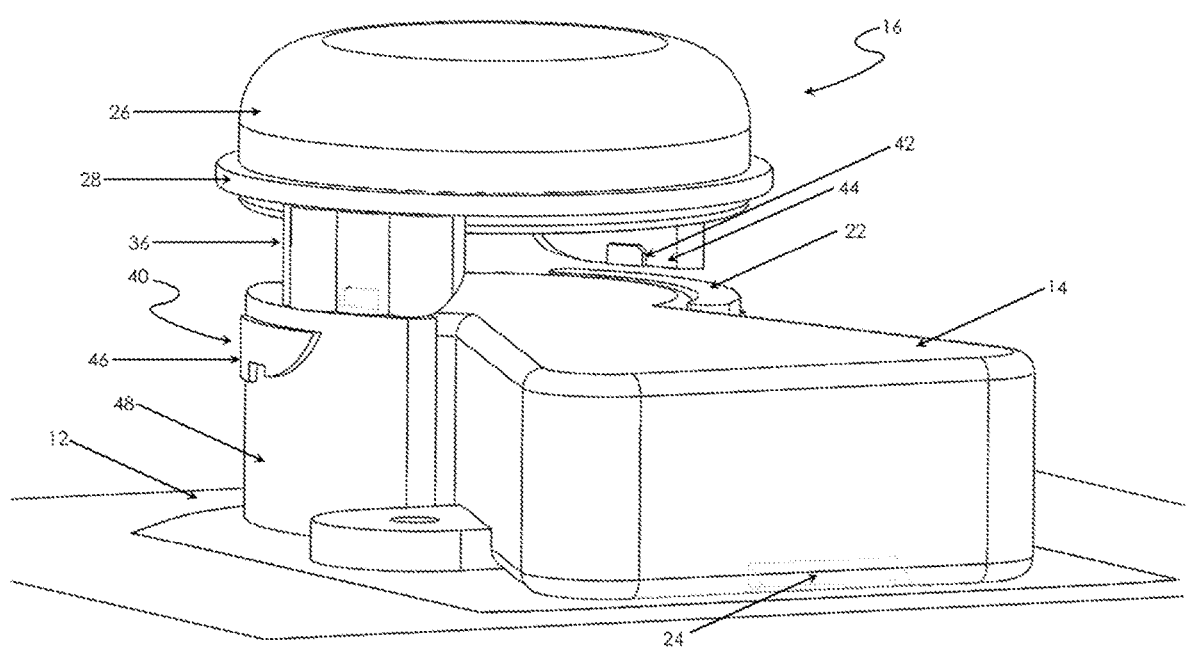
FIG. 5 illustrates a perspective view of attachment of a cap and ring assembly to a securement base with a catheter hub disposed between the cap and ring assembly and the securement base, according to an embodiment of the present invention.

FIG. 5 illustrates a perspective view of attachment of a cap and ring assembly to a securement base with a catheter hub disposed between the cap and ring assembly and the securement base, according to an embodiment of the present invention. As illustrated in FIG. 5, a portion of the catheter hub 14 has a matching geometric form to that of the space defined by vertical retentive member 22 of the securement base 12. The catheter hub 14 is horizontally stabilized by both the vertical retentive members 22 and alignment tab 24, which may exist external to an outer wall of the catheter hub 14 or fit within a recess on the distal end of the catheter hub 14, as shown in FIG. 5. Transverse securement is accomplished by the attachment of the securement assembly 16 where the cap 26 maintains relative position to the catheter hub 14 as the ring 28 engages in a rotational means. The locking mechanism 40 between the securement assembly 16 and the vertical retentive members 22 in a preferred embodiment is accomplished by locking a tab 42 located on the inner surface 44 of the securement tabs 36 with a boss 46 having matching interlocking features, such as a notch, as part of the vertical retentive members.

Figure 6:
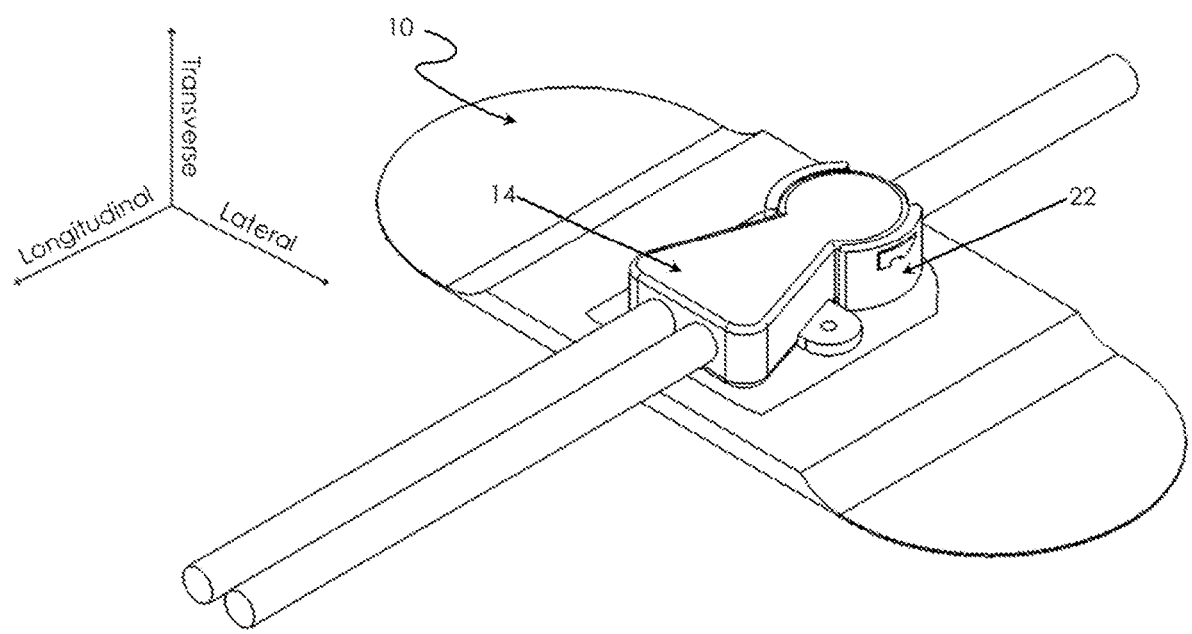
FIG. 6 illustrates a perspective view of a catheter hub disposed in a securement device in a planar direction when a cap has been removed, according to an embodiment of the present invention.

FIG. 6 illustrates a perspective view of a catheter hub disposed in a securement device in a planar direction when a cap has been removed, according to an embodiment of the present invention. The planar securement of the catheter hub 14 within the securement device 10 in the absence of a securement assembly is illustrated in FIG. 6. The vertical retentive members 22 of generally annular form prevent longitudinal movement, and partial lateral securement, whereas a plurality of alignment tabs 24 either fitting within the catheter hub 14 or disposed adjacent to, restrict all movement in the longitudinal-lateral axes.

Figure 7:
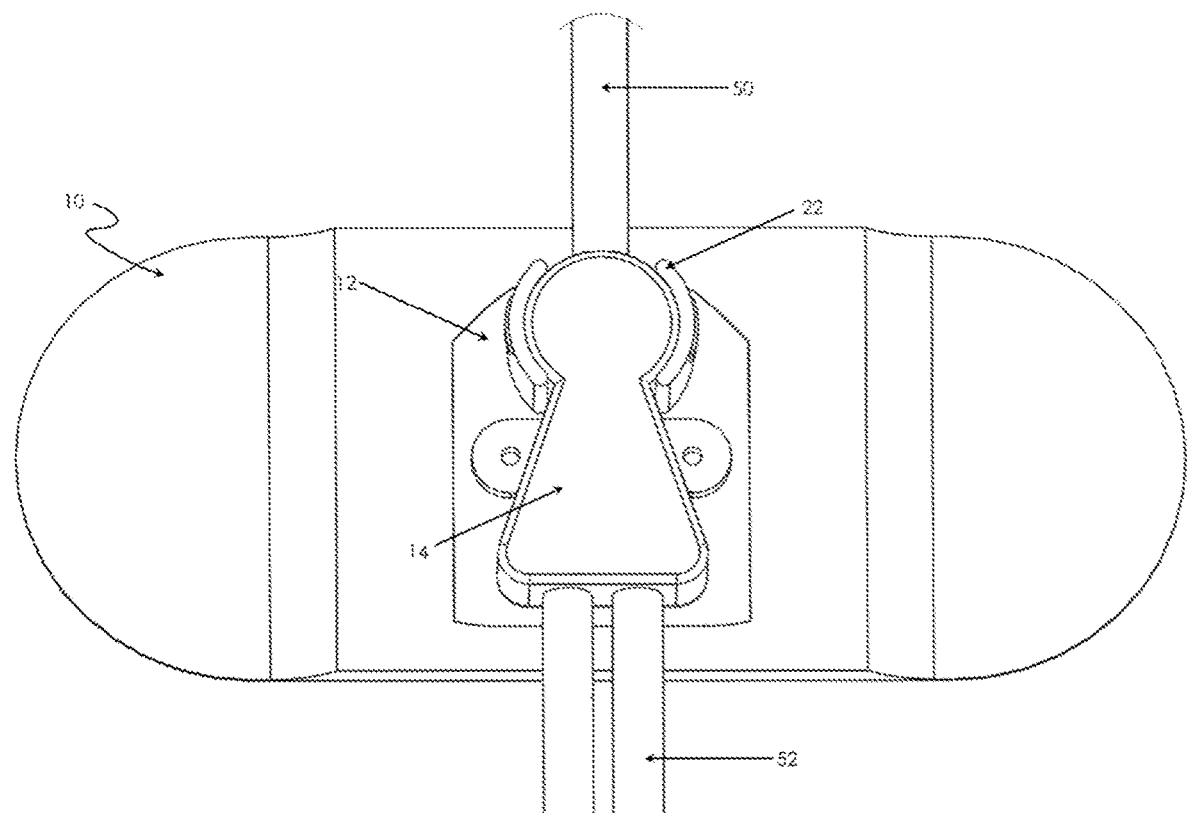
FIG. 7 illustrates a top down view of a catheter hub placed within a securement device following percutaneous insertion, according to an embodiment of the present invention.

FIG. 7 illustrates a top down view of a catheter hub placed within a securement device following percutaneous insertion, according to an embodiment of the present invention. FIG. 7 shows the catheter hub 14 placed on the securement base 10 following percutaneous insertion. The catheter hub 14 is placed within the matching features of the vertical retentive members 22 and the securement base 12 is attached to the patient's skin by an adhesive base, as is common in the art, and where the catheter hub 14 is maintained within the entirety of the securement base 12, so as to provide flexural support. A multi-lumen catheter 50 extends to the patient and the catheter extensions 52 are directed away from the patient.

Figure 8:
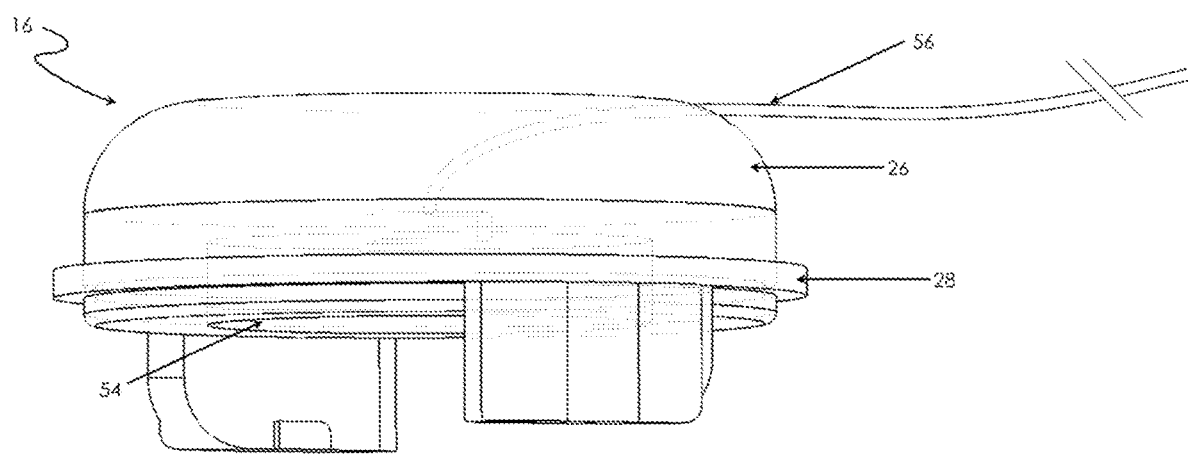
FIG. 8 illustrates a perspective view of a cap and ring assembly that incorporates an active element requiring external technology, according to an embodiment of the present invention.

FIG. 8 illustrates a perspective view of a securement assembly 16 that incorporates an active element requiring external technology, according to an embodiment of the present invention. FIG. 8 shows a securement assembly 16 incorporating an active element 54 requiring external technology such as would be provided through a flexible cable 56. The freely rotating ring 28 allows maintaining relative orientation of the cap 26, with respect to the catheter hub 14, during attachment.

Figure 9:
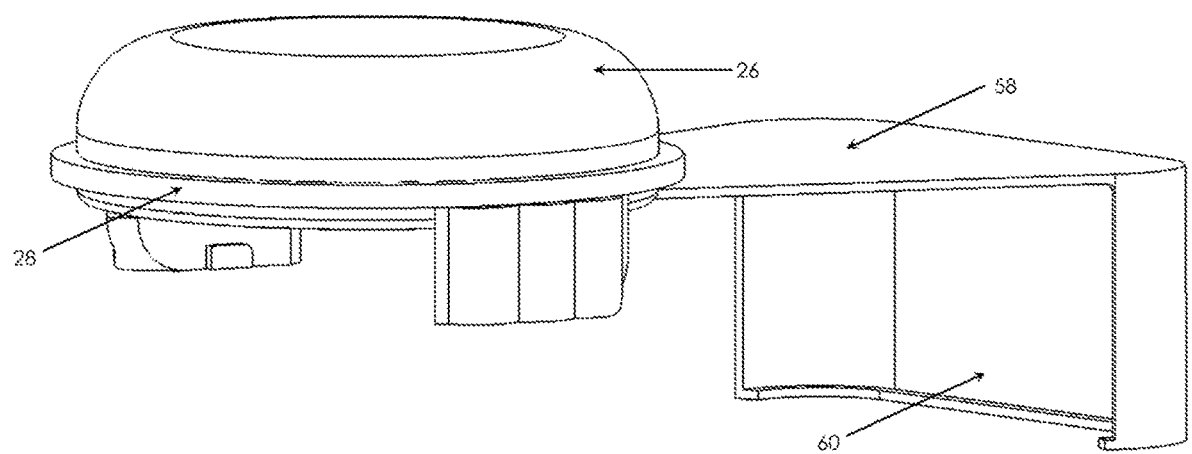
FIG. 9 illustrates a perspective view of a cap and ring assembly that incorporate a passive barrier, as would be used with a catheter hub employing removable extensions, according to an embodiment of the present invention.

FIG. 9 illustrates a perspective view of a cap and ring assembly that incorporate a passive barrier, as would be used with a catheter hub employing removable extensions, according to an embodiment of the present invention. A cap 26 is shown that incorporates a passive technology such as a protective barrier 58, such as would be used with catheter hubs using removable extensions. The protective barrier encompasses the majority of the catheter hub and contains a member that covers the region 60 where the removable extensions would be attached, while wrapping briefly under the catheter hub 14 for a secure fit. The protective barrier 58 may be attached to the cap 26 or may be placed on the catheter hub initially and secured in place by the interlocking mechanism of the ring 28.

In one embodiment, the cap contains a piezoelectric element that imparts vibrational energy to the catheter disposed between the cap and securement base. In another embodiment, the cap contains a light source, such as of the ultraviolet spectrum, which imparts germicidal UV-radiation for sterilization or disinfection of indwelling catheters. In still another embodiment, the cap contains optical components such as a photonic integrated circuit, coherent optic transceiver, and nanophotonic devices. In another embodiment, the cap contains a digital circuit such as a CMOS circuit. In another embodiment, the cap contains sensors, such as optical, chemical, physical, electrical, positional, or other sensor type. In another embodiment, the cap contains imaging components, such as spectroscopy, fluorescence, and fiber optic devices. In another embodiment, the cap contains processing elements, diagnostic tools, data logging, or other computing elements. In another embodiment, the cap contains communication devices, including any combination of transmitters or receivers. In still another embodiment, the cap contains electrical terminals which engage with the securement base and activate any of said active technologies emanating from the securement base.

It is expected that some caps may require external technology such as electrical power, computer processing, monitoring, or data communication, and in such cases the caps may have a physical cable connecting the cap to the external source. For example, a cap may include a light source and detector and require a handheld unit or monitoring device for additional technological benefit. In said example, if the active technology is not intended for continuous use, active caps may be replaced by non-tethered passive caps.

It is reasonable that caps contain one or more functional utility, and may take on the form of a disc or other shape that enables stacking or layering of one or more caps. Moreover, it is conceivable that the securement base contains two or more interlocking regions.

It is the object of the present invention to describe a securement device with modular caps of various utility to enable communication, diagnostics, treatment, and monitoring of physiologic, anatomic, and other clinically relevant properties or conditions.

In the preferred embodiment, the plurality of caps have a universal size and interlocking means that attach to a securement base with matching universal form features, and where said base and cap components are universal with regards to clinical catheters ranging from pediatric through adult, such that the interlocking means are independent of catheter size. Said assembly is adaptable to all clinical catheters of both short and long term use including, interventional, intravascular, and urethral types.

Figure 10:
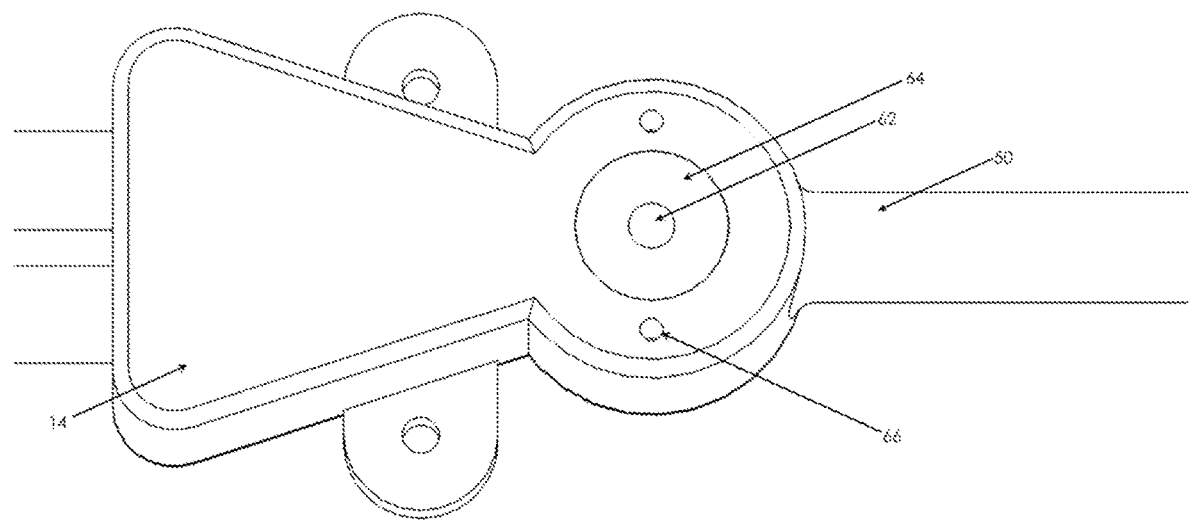
FIG. 10 illustrates a catheter hub with properties enabling coupling with the cap and ring assembly, according to an embodiment of the present invention.

FIG. 10 illustrates a catheter hub with properties enabling coupling with the cap and ring assembly, according to an embodiment of the present invention. As illustrated in FIG. 10, one example of a preferred embodiment of the catheter hub 14 with multi-lumen catheter 50 includes features such as a transparent window 62, an acoustic matching material 64, and alignment pins 66 for a securement assembly 16 requiring particular orientation during attachment.

Another object of the present invention is imparting functional value to the catheter hub. Disposed between the interlocking mechanisms of the receiving base and modular caps, the catheter hub provides a new site of connectivity. The risk of contamination to the sterile environment, such as for indwelling medical devices, is minimized when electromagnetic or acoustic energy is applied through a barrier (i.e., non-contact means), for example, through the wall of an elongated medical article such as a catheter. The present invention establishes a site of connectivity to the percutaneous catheter that allows energy to be delivered in a non-invasive, non-sterile manner.

In enabling said active technologies, the catheter hub may include one or more materials, arrangements, or other properties that support the functional utility of one or more caps, where said hub may be universal in use for certain courses of treatment (such as for both UV sterilization and ultrasonic energy) or of single utility. In this way, the active technology is distributed through, along, or by the catheter, with the hub as the technology's single source. For example, in one embodiment, the catheter hub contains a strategic material arrangement to improve acoustic matching for better coupling between caps containing a vibrating source (e.g., a piezoelectric element). In another embodiment, the hub contains a UV-transmissive region and either a light guide for directing light emanating from an external source or a diffuser for uniform light dispersion.

In still another embodiment, the hub may contain biosensors or the terminal ends of optical fibers, electrical wires, or other guiding medium, which relay measureable data to elements disposed either within the cap or hub.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A securement device for use with a percutaneous catheter, comprising:
    a base defining a top side and a bottom side, wherein the bottom side is configured for attachment to a surface, and wherein the top side defines retention walls in a predetermined geometry;
    a catheter hub having an outer wall defining the predetermined geometry, such that the catheter hub is held within the retention walls of the base; and
    a securement assembly having locking securement tabs that fit directly over an outer surface of the retention walls to lock the catheter hub to the base,
    wherein the securement assembly further comprises a cap and a locking ring, and
    wherein the locking ring is rotatable to engage the locking securement tabs and lock the catheter hub to the base.

2. The securement device of claim 1 further comprising the base defining alignment members for further constraining movement of the catheter hub.

3. The securement device of claim 1 wherein the bottom side of the base is attachable to a surface with an adhesive pad.

4. The securement device of claim 1 wherein the base is formed from a semi-flexible, polymeric material.

5. The securement device of claim 1 wherein the locking ring defines geometry configured to interlock with geometry defined by the base.

6. The securement device of claim 1 wherein the cap further defines a groove in which the locking ring is disposable.

7. The securement device of claim 6 wherein the locking ring is freely rotatable within the groove.

8. The securement device of claim 1 wherein the cap further comprises one of a group consisting of a piezoelectric element that imparts vibrational energy to the catheter disposed between the cap and securement base, a light source of the ultraviolet spectrum, which imparts germicidal UV-radiation for sterilization or disinfection of indwelling catheters, optical components including a photonic integrated circuit, coherent optic transceiver, or nanophotonic devices, a digital circuit including a CMOS circuit, sensors including optical, chemical, physical, electrical, positional, or other sensor type, imaging components including spectroscopy, fluorescence, or fiber optic devices, processing elements, diagnostic tools, data logging, or other computing elements, communication devices, including any combination of transmitters or receivers, and electrical terminals which engage with the securement base and activate any of said active technologies emanating from the securement base.

9. A method of attaching a securement device for use with a percutaneous catheter, comprising:
    disposing a catheter hub between retention walls of a base having a top side and a bottom side, wherein the top side defines the retention walls in a predetermined geometry;
    sliding locking securement tabs of a securement assembly directly over an outer surface of the retention walls, wherein the securement assembly includes a cap and a ring;
    rotating the ring of the securement assembly to engage the locking securement tabs and lock the catheter hub to the base; and
    attaching the bottom side of the base to a surface.

10. The method of claim 9, wherein the locking of the catheter hub to the base includes the locking securement tabs of the cap to the retentive walls of the base to hold the cap to the securement device and to hold the catheter hub between the securement assembly and the base.

11. The method of claim 9, wherein the bottom side of the base is attached to the surface by an adhesive base.

12. The method of claim 9, wherein the securement assembly is coupled to the base using at least one selected from the group consisting of: a push-and-twist attachment, a screw type attachment, a snap-fitting attachment, a slotted mechanism, and a frictional fit.

13. The method of claim 9, wherein the ring which is secured to the base defines geometry configured to interlock with geometry defined by the base.

* * * * *